United States Patent [19]

Bedi et al.

[11] Patent Number: 4,627,437

[45] Date of Patent: Dec. 9, 1986

[54] METHOD OF APPLYING A FASTENER TO TISSUE WITH A PAIR OF HOLLOW NEEDLES

[75] Inventors: James J. Bedi, Stockton; Donald M. Golden, Cherry Hill, both of N.J.; William P. McVay, Clearwater, Fla.

[73] Assignee: Ethicon, Inc., Somerville, N.J.

[21] Appl. No.: 741,404

[22] Filed: Jun. 5, 1985

Related U.S. Application Data

[63] Continuation of Ser. No. 506,146, Jun. 20, 1983, abandoned.

[51] Int. Cl.$^4$ .............................................. A61B 17/10
[52] U.S. Cl. .................................. 128/334 C; 128/330; 227/DIG. 1
[58] Field of Search ........... 128/346, 337, 335, 334 R, 128/334 C, 330, 325, 326, 92 B; 3/1; 227/DIG. 1, 15–18, 77; 411/469, 451, 360, 501, 506, 362–364, 455–457, 543, 518, 614, 623, 703, 297, 150 FP, 16 PB, 697, 580, 581, 584, 453, 30.5 P, 537, 515, 513, 503, 94–96

[56] References Cited

U.S. PATENT DOCUMENTS

| Re. 27,391 | 6/1972 | Merser | 24/150 FP X |
|---|---|---|---|
| 306,479 | 10/1884 | Goddard | 24/95 |
| 389,660 | 9/1888 | Mandel et al. | 411/457 X |
| 579,831 | 3/1897 | Ketchum | 24/95 |
| 1,988,233 | 1/1935 | Berendt | 24/95 |
| 2,794,981 | 6/1957 | Brayton | 227/15 |
| 2,881,762 | 4/1959 | Lowrie | 128/337 |
| 2,897,561 | 8/1959 | Megibow | 24/95 |
| 2,900,696 | 8/1959 | Bacon | 24/614 X |
| 3,009,852 | 11/1961 | Gruner | 128/330 X |
| 3,166,072 | 1/1965 | Sullivan | 128/346 X |
| 3,210,820 | 10/1965 | Humiston | 24/584 X |
| 3,326,217 | 6/1967 | Kerr | 227/DIG. 1 C X |
| 3,357,296 | 12/1967 | Lefever | 128/334 C X |
| 3,494,006 | 2/1970 | Brumlik | 411/456 X |
| 3,570,497 | 3/1971 | Lemole | 128/335.5 |
| 3,577,601 | 5/1971 | Mariani et al. | 24/16 |
| 3,683,927 | 8/1972 | Noiles | 128/326 X |
| 3,744,495 | 7/1973 | Johnson | 128/330 |
| 3,802,438 | 4/1974 | Wolvek | 128/335 |
| 3,857,396 | 12/1974 | Hardwick | 128/335 |
| 3,875,648 | 4/1975 | Bone | 227/19 X |
| 3,981,051 | 9/1976 | Brumlik | 411/456 X |
| 4,006,747 | 2/1977 | Kronenthal et al. | 128/337 X |
| 4,038,725 | 8/1977 | Keefe | 24/150 FP |
| 4,060,089 | 11/1977 | Noiles | 128/337 X |
| 4,235,238 | 11/1980 | Ogiu et al. | 128/335 X |
| 4,259,959 | 4/1981 | Walker | 128/337 |
| 4,294,255 | 10/1981 | Geroc | 128/334 C |
| 4,326,531 | 4/1982 | Shimonaka | 128/326 |
| 4,400,833 | 8/1983 | Kurland | 3/1 |
| 4,402,445 | 9/1983 | Green | 128/334 R X |
| 4,454,875 | 6/1984 | Pratt et al. | 128/92 B |

FOREIGN PATENT DOCUMENTS

| 1097171 | 3/1981 | Canada | 128/330 |
|---|---|---|---|
| 1385691 | 12/1964 | France | 40/300 |
| 8301190 | 4/1983 | Int'l Pat. Institute | 227/DIG. 1 |
| 82738 | 10/1919 | Switzerland | 128/330 |
| 972731 | 10/1964 | United Kingdom | 128/346 |

Primary Examiner—Michael H. Thaler
Attorney, Agent, or Firm—Robert L. Minier

[57] ABSTRACT

A pair of parallel, hollow needles are provided for receiving a tissue fastener of the type having at least a fastening member with a pair of legs joined by a link. Each needle has an internal passage extending from a fastening member receiving end to a discharge end. Each needle also has a slot extending along its length in communication with the passage and facing the slot of the other needle. A leg of the fastening member is placed in each needle with the fastening member link extending through the needle slots between the needles. The instrument has an anvil for being located on one side of the tissues opposite the needles. The needles are inserted through the tissues towards the anvil. Then the fastening member is pushed through the needles by a drive member so that at least a portion of the fastening member link lies against one side of the tissues and so that at least a portion of each of the fastening member legs is located and secured on the other side of the tissues.

1 Claim, 19 Drawing Figures

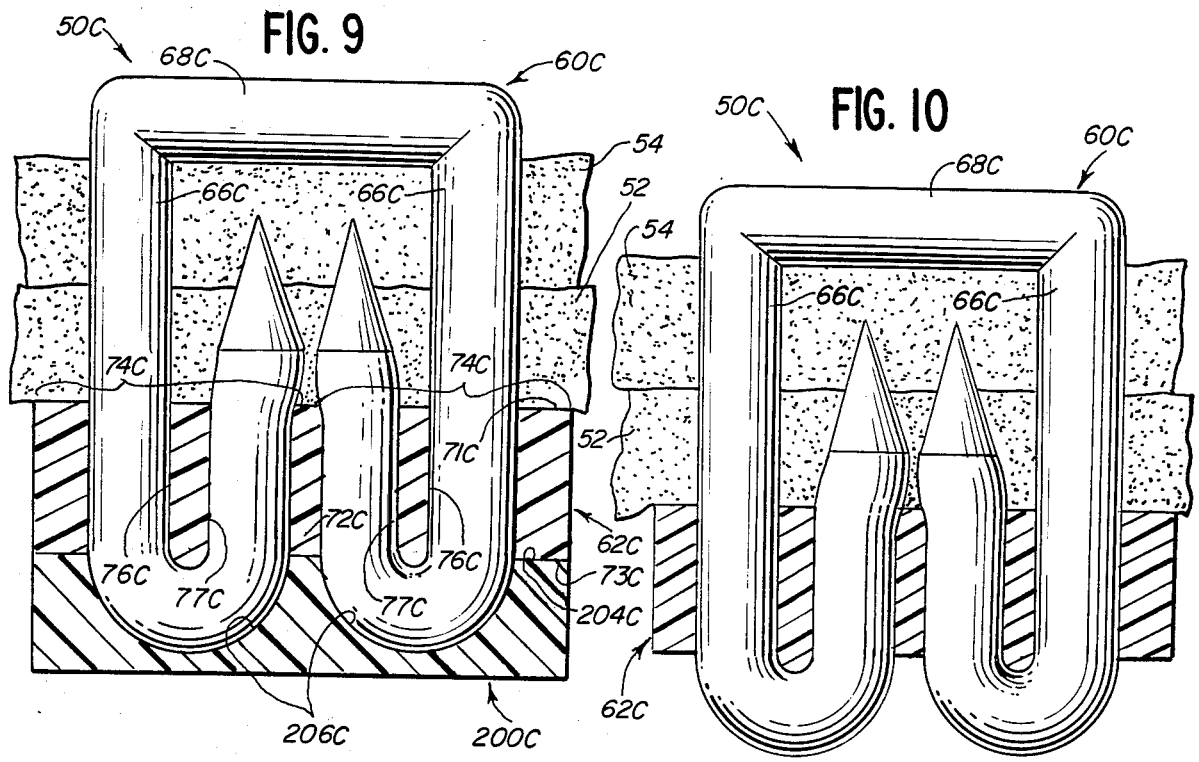
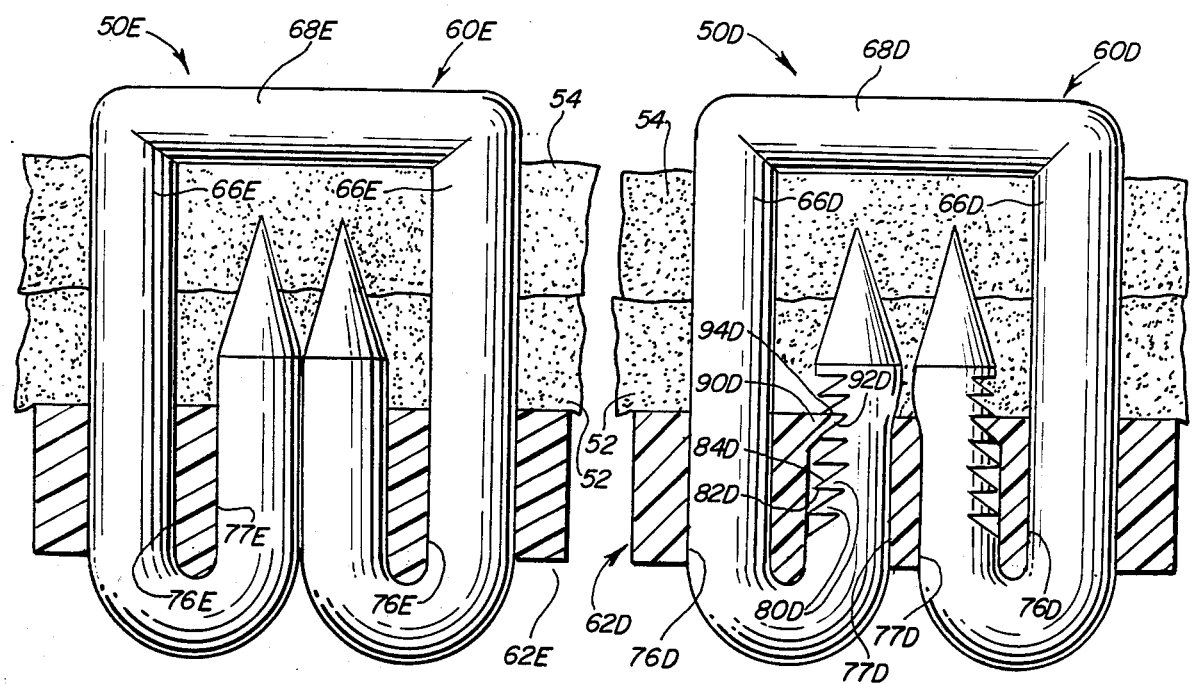

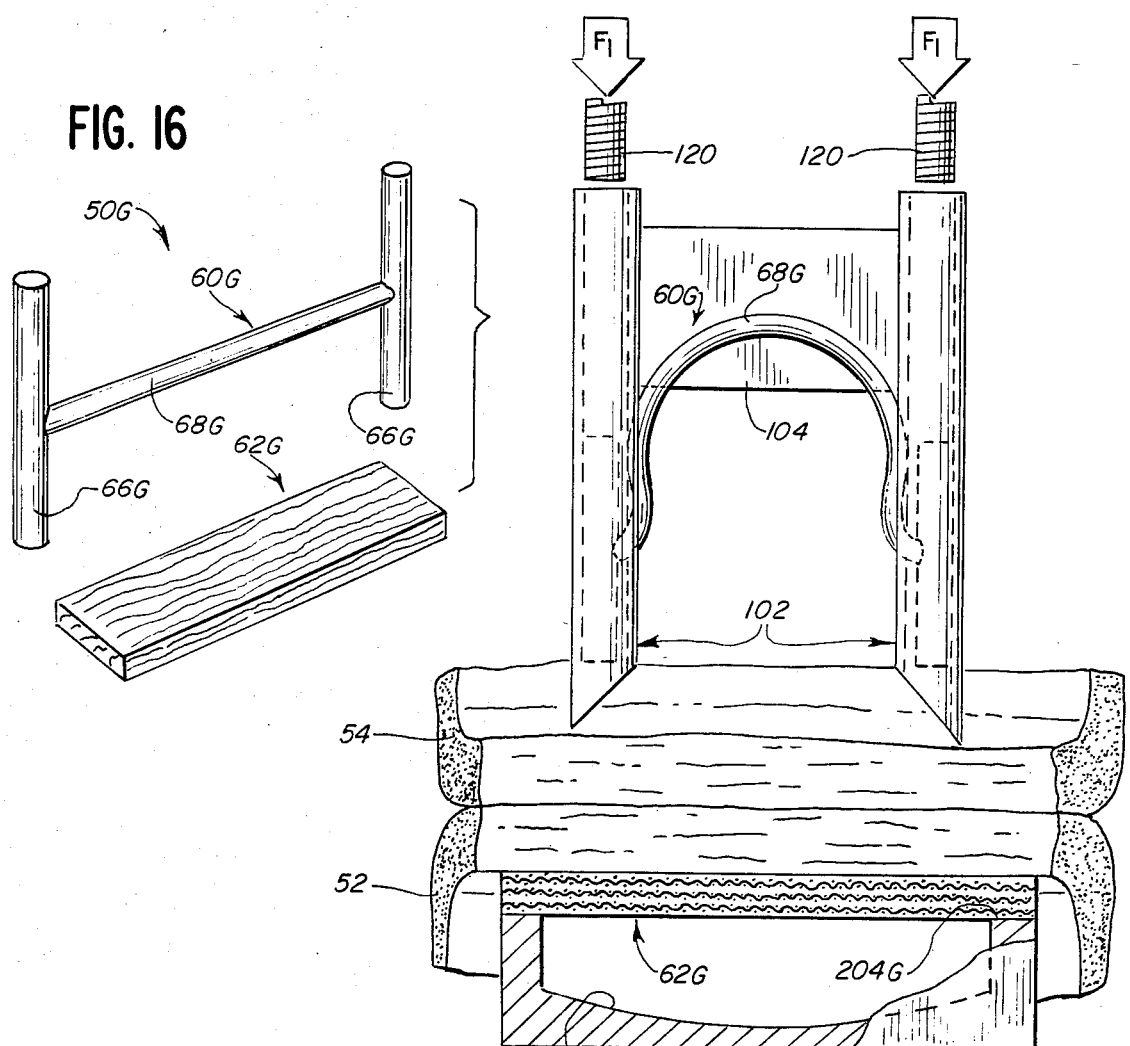
FIG. 16
FIG. 17
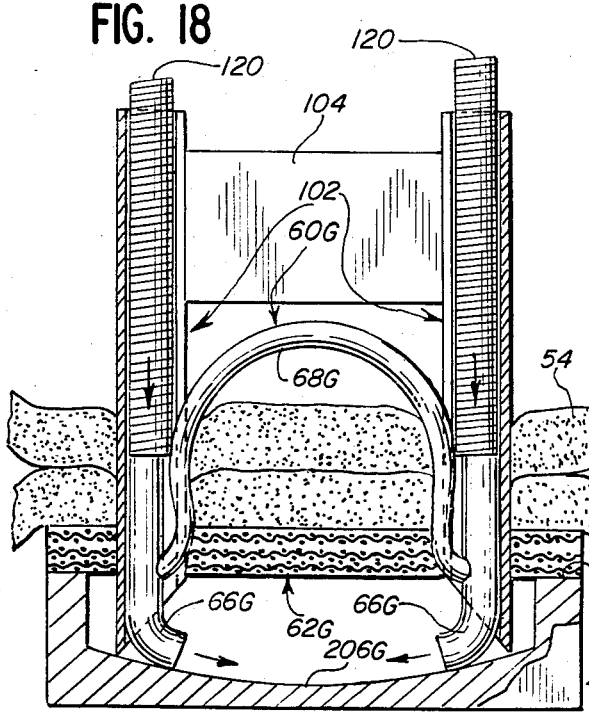
FIG. 18
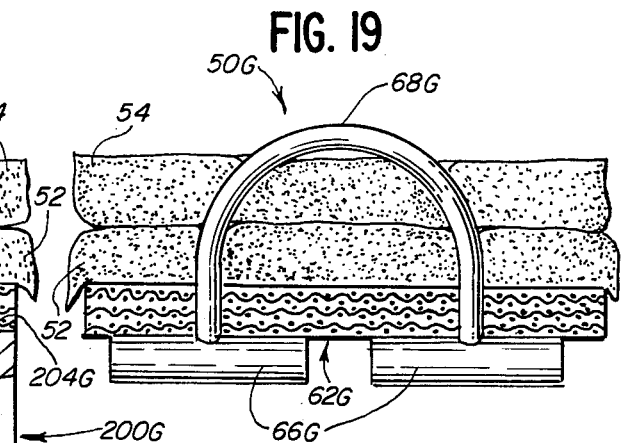
FIG. 19

METHOD OF APPLYING A FASTENER TO TISSUE WITH A PAIR OF HOLLOW NEEDLES

This is a continuation of application Ser. No. 506,146, filed June 20, 1983, abandoned.

TECHNICAL FIELD

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International Patent Application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined by a link to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The fastener strip prongs each include a plurality of spaced-apart engaging members for engaging the retainer strip at a desired position relative to the prongs. This provides for the capability of adjusting the distance between the fastener strip and the retainer strip. Such a fastening device may be fabricated from a biodegradable or absorbable material.

Other patents, such as U.S. Pat. Nos. 2,286,578 and 3,638,654, disclose instruments for applying flexible sutures with needles that are inserted into the tissue portions.

Other types of fasteners that include a fastening member with legs joined by a link and secured in a retaining receiver on one side of an incision are disclosed in the following concurrently filed, copending U.S. patent applications assigned to the assignee of the instant application.

(1) Ser. No. 506,151, entitled "Two-Piece Tissue Fastener With Coinable Leg Staple And Retaining Receiver And Method And Instrument For Applying Same";

(2) Ser. No. 506,088, entitled "Two-Piece Tissue Fastener With Toothed Leg Staple And Retaining Receiver"; and (3) Ser. No. 506,083, entitled "Two-Piece Tissue Fastener With Bent Leg Staple And Retaining Receiver";

(4) Ser. No. 506,087, entitled "Two-Piece Tissue Fastener With Non-Reentry Bent Leg Staple And Retaining Receiver";

(5) Ser. No. 506,082, entitled "Two-Piece Tissue Fastener With Compressible Leg Staple And Retaining Receiver";

(6) Ser. No. 506,145, entitled "Two-Piece Tissue Fastener With Wedged Leg Staple And Retaining Receiver"; and (7) Ser. No. 506,144, entitled "Two-Piece Tissue Fastener With Deformable Retaining Receiver".

The fasteners disclosed in the above-identified copending patent applications are also illustrated and briefly described herein. These fasteners may be applied to the tissue portions by forcing the fastening members directly into the tissue portions with a suitable instrument so that the fastening member legs protrude from the tissue portions on one side of the incision where they are engaged by the receiver.

When the fastening member legs are forced through the tissue portions, care must be taken to prevent deflection of the legs by the tissue. Such deflection could prevent receipt of the legs in the fastener. Although these fasteners work well in many applications, in some situations, as with relatively tough tissue and relatively slender legs, prevention of such deflection may be difficult.

U.S. Pat. No. 4,006,747 discloses the application of a flexible fastener to tissue by means of a slotted, hollow, straight, needle with a plunger for pushing the fastener through the needle. The application of a similar fastener in a non-surgical situation is disclosed in U.S. Pat. No. 4,215,807.

This type of fastener, for use in joining tissue, is also disclosed in the pending patent application Ser. Nos. 506,151, 506,088, 506,083, 506,087, 506,082, 506,145, and 506,144, filed June 20, 1983, June 20, 1983, June 20, 1983, June 20, 1983, June 20, 1983, June 20, 1983, and June 20, 1983, respectively, which are all assigned to the assignee of the instant application. This type of fastener comprises a pair of anchoring means or legs joined by a flexible link or filament. Each leg or anchoring means has two ends and is connected intermediate of its two ends to the filament or link. These pending applications also identify U.S. patents disclosing other types of fasteners, along with methods and instruments for applying such other types of fasteners.

According to the methods disclosed in the pending patent applications identified in the preceding paragraph, an instrument having a single, hollow, slotted, curved needle is used for applying the fastener. The tissue portions to be joined are overlapped in face-toface relationship and penetrated from one side of the wound or incision by the needle. The needle is inserted so that the distal end of the needle projects from the other side.

One of the fastener legs is inserted into the needle on the first side of the wound or incision and is pushed through the needle so that the one leg is discharged from the needle on the other side of the wound or incision. Then the needle is pulled back out of the tissue leaving the fastener in the tissue with the link transversing the wound or incision through the tissue portions and with the legs lying on either side of the wound or incision.

U.S. Pat. No. 3,716,058 discloses a barbed surgical suture and a special needle used for inserting the suture in position within tissue. The needle is hollow and has a lengthwise notch or channel for carrying the suture. The needle, with one end of the suture mounted therein, is inserted into the tissue and then the needle is removed rearwardly from the tissue to leave the one end of the suture in the tissue. The same procedure is then repeated for the other end of the suture.

A non-surgical method and apparatus are disclosed in U.S. Pat. No. 3,875,648 for applying a similarly shaped flexible fastener to hold two layers of garment material together. The apparatus includes a pair of hollow, slotted needles, each with a reciprocative pusher member disposed therein.

The fastener is applied by placing each leg in one of the hollow slotted needles on a first side of the material layers and penetrating the material layers with the needles. Next, the legs are pushed through the needles to the other side of the material layers with a portion of the fastener filament remaining on the first side of the material layers to hold the layers together after withdrawal of the needles.

Although many of the above-discussed types of tissue fastening devices and techniques are satisfactory in various applications, there is a need to provide an improved method for fastening mammalian tissue with reduced trauma.

It would also be desirable to provide an improved fastening method for use with fasteners fabricated from absorbable materials that can provide primary approximation of the tissue edges to insure that the tissue edges are in continuous contact. Further, such an improved method should provide a desired amount of hemostatic compression to minimize bleeding, but allow some collateral blood circulation to the wound or incision edges of the tissue to promote healing. In addition, such an improved method should have the capability to accommodate varying tissue thicknesses and should leave as little tissue cuff or margin as possible in effecting the joining of the tissue.

Further, it would be beneficial if such an improved fastening method was compatible with fasteners that are fabricated with (1) as small a size as possible to minimize dosage, (2) a minimum of sharp edges or protrusions, and (3) a configuration that does not form, or contribute to the formation of, pockets of infection in the tissue.

Further, such an improved fastening method would desirably provide the surgeon with tactile feedback and compensating control during the application of the fastener.

It would also be advantageous to provide a fastening method that would readily accommodate application by means of an appropriately designed instrument.

Finally, it would be desirable to provide a relatively simple, yet effective and rapidly operating instrument for applying a variety of fasteners according to such an improved method. When used to apply two legged fastening members to tissue with retaining receivers, such an instrument and improved method should desirably prevent deflection of the fastening member legs passing through the tissue and should provide proper alignment of the fastening member legs with the receiver.

SUMMARY OF THE INVENTION

A method and instrument are provided for applying a fastener or a group of fasteners to close a wound or incision in mammalian tissue by holding together portions of the tissue defining the wound or incision so as to facilitate healing of a wound or incision. The method can be employed with a variety of those types of fasteners comprising at least a fastening member having a pair of legs joined by a link. Such a fastener is adapted to remain in the tissue portions with at least a portion of the link lying substantially against one of the tissue portions on one side of the wound or incision and with at least a portion of each of the legs being restrained or secured adjacent another of the tissue portions on the other side of the wound or incision.

The method requires the use of an instrument having a pair of spaced-apart needles oriented in generally parallel planes. Each needle has a distal end adapted for piercing the tissue portions. Each needle further is hollow and has a passage extending along its length from a fastening member receiving opening to a discharge opening at the distal end of the needle. Each needle further defines a slot extending along its length in communication with the passage and facing the slot of the other needle.

When applying a fastener according to the method, two or more tissue portions are approximated in a generally face-to-face relationship. Then, the needles are inserted through the approximated tissue portions to locate the receiving openings on one side of the wound or incision and to locate at least portions of the discharge openings on the other side of the wound or incision.

Before, during, or after the step of inserting the needles into the tissue portions, the fastening member is loaded into the needles through the needle receiving openings. The fastening member is oriented with each of the legs disposed in one of the needle passages and with the link extending through the needle slots between the needles.

Next the fastening member is urged along the needles to locate at least a portion of the link on one side of the wound or incision adjacent one of the tissue portions and to locate at least a portion of each leg on the other side of the wound or incision where it is restrained or secured adjacent another of the tissue portions.

Finally, the needles are withdrawn from the tissue portions and the fastener remains holding together the tissue portions.

This method and instrument may be used for the variety of such types of fasteners. Numerous other features of this novel method and instrument will be apparent from the following detailed description and accompanying drawings.

BRIEF DESCRIPTION OF THE DRAWINGS

In the accompanying drawings forming part of the specification, and in which like numerals are employed to designate like parts throughout the same.

FIG. 9 is a view similar to FIG. 8 but showing a third embodiment of a fastener with a cooperating leg guide member temporarily in place;

FIG. 10 is a view similar to FIG. 9 but showing the third embodiment of the fastener after the leg guide member has been removed from the site;

FIG. 11 is a view similar to FIG. 10 but showing a fourth embodiment of a fastener;

FIG. 12 is a view similar to FIG. 10 but showing a fifth embodiment of a fastener;

FIG. 16 is a perspective view of a seventh embodiment of a fastener;

FIGS. 17 and 18 are each a fragmentary, partial, cross-sectional view of two portions of mammalian tissue defined by an incision or wound showing the seventh embodiment of the fastener of FIG. 16 being inserted into the two portions of tissue with the instrument of FIG. 5; and FIG. 19 is a view similar to FIG. 18 but showing the tissue portions after the instrument has been removed from the site with the fastener fully engaged in the tissue portions.

DESCRIPTION OF THE PREFERRED EMBODIMENTS

Figure 1:
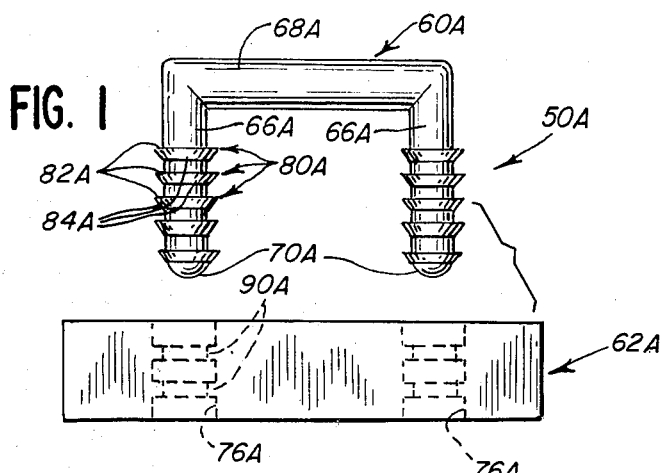
FIG. 1 is a side view of a fastening member and receiver which together comprise a first embodiment of a fastener that can be applied to tissue according to the novel method disclosed herein.

The disclosed method and instrument may be employed in different ways with a variety of fasteners. The specification and accompanying drawings disclose only a few specific forms of an improved method and of an improved fastener applying instrument as illustrative examples. The precise shapes and sizes of the various fasteners and fastener applying instrument components herein described are not essential to the invention unless otherwise indicated. The disclosed method and instrument are not intended to be limited for use with the fastener embodiments illustrated, and the scope of the invention will be pointed out in the appended claims.

FIRST EMBODIMENT OF THE FASTENER

A first embodiment of a fastener that may be applied according to the novel improved method is illustrated in FIGS. 1-4 and is designated generally therein by reference numeral 50A.

Figure 4:
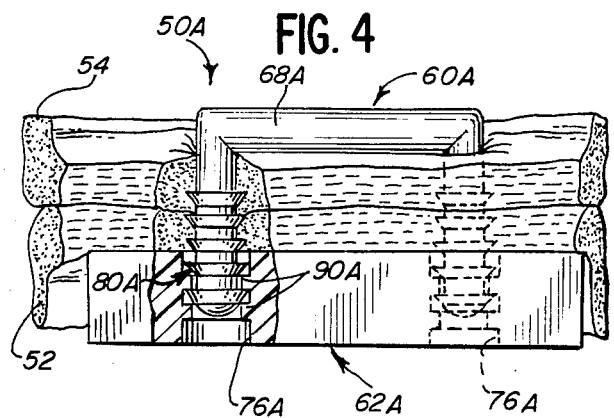
FIG. 4 is a fragmentary, perspective, partial cross-sectional view of two portions of mammalian tissue defined by an incision or wound and being held together by the assembled fastener of FIG. 1 with some of the tissue portions cut away to better illustrate interior detail.

The fastener 50A is illustrated in FIG. 4 in the fully assembled, "set" configuration wherein it is shown holding together two portions 52 and 54 of mammalian tissue, such as are defined by a wound or incision, to facilitate healing of the wound or incision. Typically, a plurality of such fasteners 50A would be used to close a wound or incision. However, with just a small wound or incision, one fastener 50A may be sufficient.

The fastener 50A includes two components, a generally U-shaped or open loop fastening member 60A and a receiver 62A, which are initially separated as illustrated in FIG. 1 and which are adapted to cooperate to compress or hold between them the tissue portions.

Figure 2:
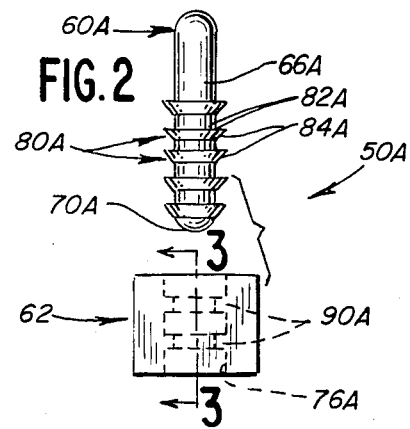
FIG. 2 is an end view of the fastening member and receiver of FIG. 1.

As is best illustrated in FIGS. 1, 2 and 4, the fastening member 60A includes, (1) a pair of anchoring means or legs 66A adapted to be passed at least partially through the tissue portions and (2) a filament, link, or link member 68A which is connected to the legs 66A and which is adapted to lie substantially against one of the tissue portions (e.g., tissue portion 54 in FIG. 4). The legs 66A of the fastening member are generally parallel to each other and are generally perpendicular to the link 68A. Preferably, each leg 66A has a solid, generally cylindrical configuration with a rounded end 70A. The link 68A may be cylindrical (as illustrated) or may have any other suitable shape (such as that of a regular parallelpiped, for example).

As best illustrated in FIGS. 1-4, the receiver 62A defines at least one passage 76A for receiving one of the fastening member legs 66A and at least one other passage 76A for receiving the other fastening member leg 66A. Each receiving passage 76A and the receiver wall that defines the passage 76A cooperate as means for receiving and encompassing at least a portion of one of the fastening member legs 66A after the leg has been inserted through the tissue portions as best illustrated in FIG. 4.

The fastener 50A is provided with unique means for effecting engagement between the fastening member 60A and the receiver 62A and for holding the fastening member 60A and receiver 62A in a desired relationship to compress between them the two tissue portions 54 and 52 as illustrated in FIG. 4 Specifically, as best illustrated in FIGS. 1 and 2, each leg 66A of the fastening member 60A defines a plurality of spaced-apart, resilient locking members 80A on its exterior along at least a portion of its length.

As best illustrated in FIG. 1, each locking member 80A has a frustoconical configuration presenting an upper, annular locking edge or surface 82A oriented generally normal to the longitudinal axis of the fastening member leg 66A. Each locking member 80A also has a lower, frustoconical engagement surface 84A. Each locking member 80A is somewhat inwardly flexible when force is applied to the surface 84A of the locking member to act in a direction along the length of the leg 66A away from the distal end of the leg. However, each locking member 80A is resistant to inward flexing when force is applied to the annular edge or surface 82A of the locking member 80A to act in the direction along the length of the leg toward the distal end of the leg. This feature, the utility of which will become apparent hereinafter, exists, in part, as a result of the particular configuration of the member 80A as defined by the surfaces 82A and 84A.

Figure 3:
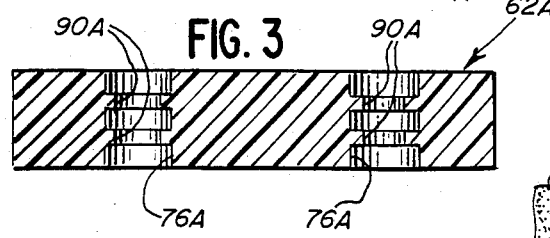
FIG. 3 is a cross-sectional view of the receiver taken generally along the plane 3—3 in FIG. 2.

The receiver 62A is provided with unique structural elements to cooperate with the teeth 80A of the fastening member 60A. Specifically, as best illustrated in FIGS. 1-3, each receiving passage 76A is generally cylindrical and is provided with one or more inwardly projecting annular flanges 90A. Each flange 90A can function as means for (1) flexing the leg locking members 80A inwardly on one leg 66A of the fastening member 60A when the one leg is being inserted through the tissue portions and into the receiver passage 76A and (2) for engaging one of the leg locking members 80A to prevent withdrawal of the leg from the receiver 62A after the leg has been received therein as best illustrated in FIG. 4.

The fastening member 60A and receiver 62A may be formed from suitable materials, such as thermoplastic polymer materials that are absorbable by mammalian tissue.

METHOD AND INSTRUMENT FOR APPLYING FASTENERS

A novel method and instrument may be used for applying fasteners, such as the first embodiment of the fastener 50A described above, to close a wound or incision in mammalian tissue by holding together two or more portions of the tissue defining the wound or incision so as to facilitate healing of the wound or incision. The method and instrument may be employed to apply fasteners of the type comprising at least a fastening member having a pair of anchoring means or legs joined by a link (e.g., such as fastening member 60A of the first embodiment of fastener 50A described above with reference to FIGS. 1-4).

Such a fastener is adapted to remain in the tissue portions with at least a portion of the link lying substantially against one of the tissue portions on one side of the wound or incision and with at least a portion of each of the legs being retained or secured adjacent another of the tissue portions on the other side of the wound or incision.

The method and instrument may be used to apply a fastener of the type that does not include a receiver as well as a fastener of the type that includes a receiver (e.g., such as receiver 62A of the first embodiment of the fastening member 50A described above with reference to FIGS. 1-4). In some designs, the receiver is necessary to retain portions of the fastening member legs on one side of the wound or incision. In other designs, the receiver merely aids in retaining the fastening member legs.

Figure 5:
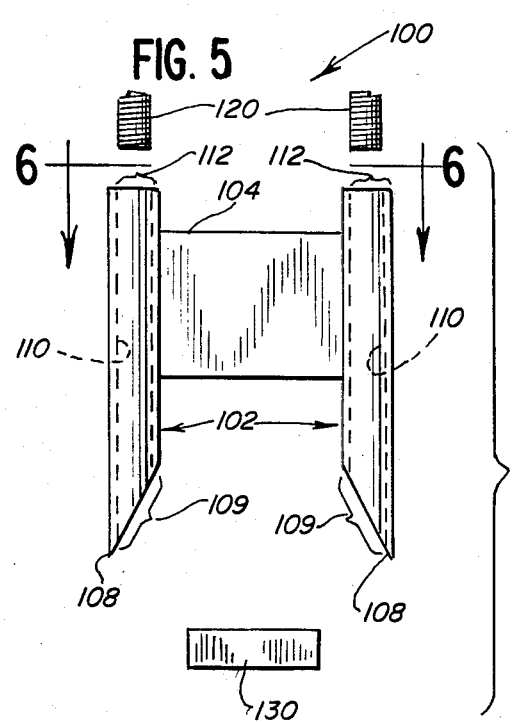
FIG. 5 is a fragmentary front view of a simplified form of an instrument for applying the first embodiment of the fastener illustrated in FIG. 1 according to the method disclosed herein.
Figure 6:
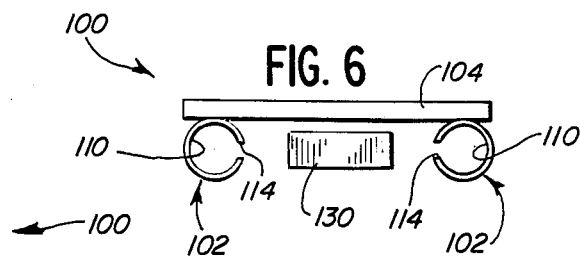
FIG. 6 is a view taken along the plane 6—6 in FIG. 5.

In applying the fastener according to this method, a novel instrument is employed. Such an instrument is illustrated in FIGS. 5 and 6 wherein it is designated generally by the reference numeral 100. The instrument 100 is illustrated in a simplified manner in FIGS. 5 and 6 to illustrate the basic components in a way that facilitates a straightforward description of the method of applying a fastener with such an instrument.

The instrument 100 includes a pair of spaced-apart needles 102 oriented in parallel planes. The needles 102 are preferably connected together by suitable means, such as a connecting plate 104. The connecting plate 104 is merely illustrative of a suitable structure for maintaining the two needles 102 in the spaced-apart, parallel relationship. Other suitable structures, including other members or housings (not illustrated) for instrument 100, may serve the same function as the plate 104 and may also function as means by which the instrument 100 may be grasped and manipulated by the surgeon.

In the illustrated embodiment in FIGS. 5 and 6, the needles 102 are generally straight and have a hollow, cylindrical configuration. The longitudinal axes of the needles 102 are parallel.

Each needle 102 is preferably provided with a distal end 108 which is angled, slanted, or pointed to aid in penetrating the tissue portions. The distal end 108 of each needle 102 defines a discharge opening 109 which communicates with an internal, cylindrical passage 110 extending along the length of the needle 102. The passage 110 extends to a fastening member receiving opening 112 (FIG. 5) at the top end of the needle 102 opposite the distal end 108. Each needle 102 also defines a slot 114 extending along its length in communication with the passage 110. The slot 114 of one of the two needles 102 faces the slot 114 of the other needle 102 as is best illustrated in FIG. 6.

A means is provided for moving the fastening member 60A along the needles. This may take the form of two drive members 120 which are each adapted to enter the fastening member receiving opening 112 of one of the needles 102 and to travel the length of the passage 110. The drive members 120, having a cylindrical shape in this illustrated embodiment, function to apply force to the fastening member so as to urge the fastening member along the needles 102 and into the receiver 62A. The drive members 120 may be rigid or flexible and may have other suitable shapes.

An anvil 130 is provided below the needles 102 and functions as a means for applying a reaction force to the tissue portions and for preventing the tissue portions from moving excessively when penetrated by the needles 102. Further, with some types of fasteners, the anvil 130 can function to hold the receiver (e.g., receiver 62A of the first embodiment of the fastener 50A described above with reference to FIGS. 1-4) against one of the tissue portions.

The instrument 100 may further include a suitable housing and mechanism (not illustrated) for effecting relative movement between (1) the anvil 130 and the needles 102 and (2) between the drive members 120 and the needles 102. Such a mechanism may include a pair of scissors-like handles with appropriate actuating mechanisms and/or linkages operably connecting the handles with the the needles, drive members, and anvil.

Figure 7:
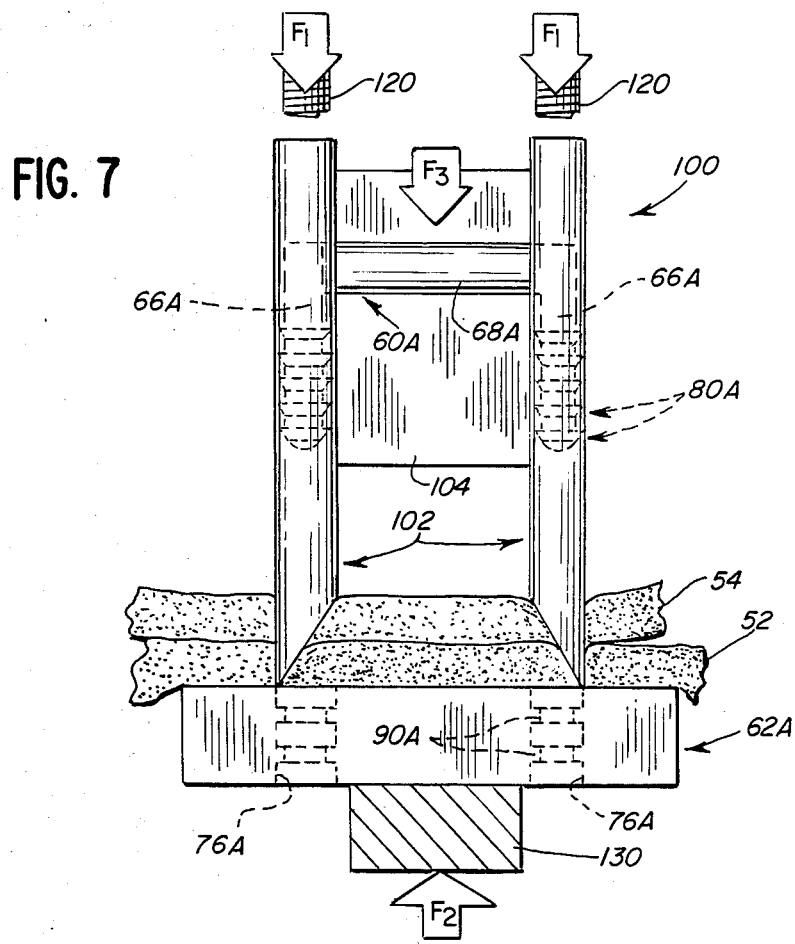
FIG. 7 is a fragmentary, partial, cross-sectional view of two portions of mammalian tissue defined by an incision or wound illustrating the employment of the instrument illustrated in FIGS. 5 and 6 to apply the first embodiment of the fastener illustrated in FIG. 1 according to the method disclosed herein.

The method of applying a fastener with the instrument 100 is best illustrated in FIG. 7 where the instrument 100 is shown applying the first embodiment of the fastener 50A described above with reference to FIGS.

1-4. Typically, the instrument 100 would first be loaded with a fastening member 60A. This would be effected by disposing the fastening member 60A in the pair of needles 102 so that the fastening member legs 66A each enter one of the needle passages 110 (FIG. 5) through the receiving opening 112 at the top of the needle. The fastening member link 68A then extends between the needles 102 and through the needle slots 114 as best illustrated in FIG. 7. The drive members 120 may then be positioned to enter the needle passages 110 through the receiving openings 112 behind the fastening member 60A.

The receiver 62A is also loaded on the instrument 100. The receiver 62A is suitably disposed on the anvil 130 in spaced relationship from the distal ends of the needles 102, but generally in alignment with the needles 102. Specifically, the receiver passages 76A are positioned to ultimately align with the needles 102 and with the fastening member legs 66A disposed within the needles 102.

Before the instrument 100 is brought into contact with the tissue portions 52 and 54, the tissue portions are first approximated in a generally face-to-face relationship as illustrated in FIG. 7. If more than two tissue portions are to be joined, they are placed side by side in generally the same manner.

Then the instrument 100 is manipulated to insert the needles 102 through the approximated tissue portions 52 and 54 in a manner which locates the receiving openings 112 on one side of the wound or incision and which locates at least portions of the needle discharge openings 109 on the other side of the wound or incision.

Prior to inserting the needles 102 into the tissue portions, or at the same time, the anvil 130 is urged toward the tissue portion 52 to bring the receiver 62A into contact with the tissue portion 52. As the needles 102 penetrate the tissue portions, the receiver 62A prevents the tissue portions from being carried with the needles 102 an excessive amount and thus permits relative movement to eventually be effected between the needles and the tissue portions.

When the tips or distal ends 108 of the needles 102 pass completely through the tissue portions, the needle tips impinge upon the upper surface of the receiver 62A at the edge of the passages 76A. Further relative movement between the tissue portions and the needles is thus prevented. At this point, the receiver passages 76A are in alignment with the passages 110 of the needles 102 for receiving the fastening member legs 66A.

Although the fastening member 60A would typically be inserted into the needles 102 prior to the tissue portions being penetrated by the needles as described above, such a sequence of operation is not necessary. Rather, the needles 102 may initially penetrate the tissue portions without the fastening member 60A being disposed in the needle passages. Then, after the tissue portions have been penetrated by the needles, the fastening member 60A may be disposed within the needles (as illustrated in FIG. 7).

In any case, after the receiver 62A has been positioned adjacent one of the tissue portions 52 and after the needles 102 have penetrated the tissue portions 54 and 52 as illustrated in FIG. 7, the fastening member 60A is next urged along the needles 102. This may be accomplished by moving the drive members 120 downwardly into the needle passages and into engagement with the fastening member 60A.

Continued movement of the drive members 120 urges the fastening member 60A along the needles so that the fastening member legs 66A are at least temporarily deformed (i.e., the locking members 80A are deflected) as the legs pass through and become disposed within the passages 76A of the receiver 62A. Typically, the relative movement between the fastening member 60A and the receiver 62A is terminated when the fastening member link 68A is at a desired distance from the receiver 62A. Preferably, this movement is terminated after the tissue portions 54 and 52 have been compressed together a desired amount as illustrated in FIG. 4. At this point, the fastening member legs 66A have become retained, secured, or locked in the receiver 62A adjacent the tissue portion 52 by engagement of the fastening member leg locking members 80A with the receiver flanges 90A in the manner described above with reference to FIGS. 1-4.

During the movement of the fastening member 60A along the needles 102, the receiver 62A is held in the proper location against the tissue portion 52 by means of anvil 130 to prevent the receiver 62A from being moved away from the tissue portions as the fastening member legs 66A are driven into the receiver 62A.

In order to effect the necessary penetration of the tissue portions 52 and 54 by the needles 102, force must be applied to the needles 102 or to the needle housing structure, such as to plate 104. Also, a substantially oppositely directed force is preferably applied to the receiver 62A. FIG. 7 illustrates the application of these forces wherein the needles 102 are each shown being moved through the tissue along the longitudinal axes of the needles with a force $F_1$. On the opposite side of the wound, the receiver 62A is held against the tissue portion 52 by means of the anvil 130 under the influence of a force $F_2$.

After needle penetration, a force can be applied to the fastening member 60A with the drive members 120 along the longitudinal axes of the needles or by a suitable drive member (not illustrated) acting just on the link 68A. Such a suitable drive member could apply a force $F_3$ to the midpoint of the link 68A to drive the fastening member 60A along the needles and into the receiver 62A.

After the fastening member 60A has been driven into the receiver 62A the desired amount, the needles 102 are withdrawn from the tissue portions and the anvil 130 is removed from the receiver 62A. The entire instrument 100 is removed from the site to leave the fastener 50A holding together the tissue portions.

Although the instrument 100 is illustrated in FIGS. 5 and 6 as having two straight needles 102, it is to be realized that the needles 102 may be curved if desired. Such curved needles would be useful in certain applications (e.g., the closure of tissue in some fascia or internal organs). Even if the needles are curved, the needles are still preferably oriented in parallel planes to accommodate the fastening member 60A which has a fixed length link 68A.

If the fastening member 60A is fabricated from an elastic material that provides a certain amount of stretch to the link 68A, then the needles 102 would not necessarily have to lie in strictly parallel planes since the link 68A could stretch, contract, or bend to accommodate the minor variations in distance between the needles along the length of the needles.

In some situations, the fastening member legs 66A may project beyond the bottom of the receiver 62A. If desired, the projecting leg portions may be severed flush with the bottom of the receiver by a suitable cutter mechanism (not illustrated) on the instrument 100.

The above-described method and instrument may be employed to apply other types of fasteners to tissue portions. Examples of other types of fasteners that may be applied with the method of the present invention will next be described.

SECOND EMBODIMENT OF THE FASTENER

Figure 8:
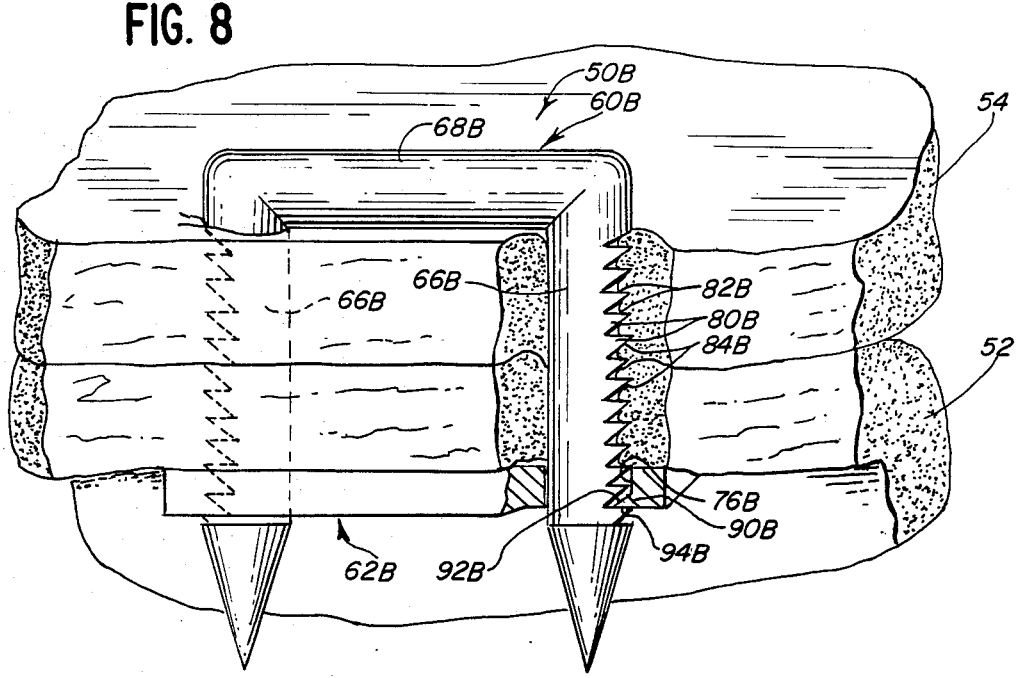
FIG. 8 is a view similar to FIG. 4 but showing a second embodiment of a fastener holding together two tissue portions defined by an incision or wound.

A second embodiment of a fastener that may be applied with the above-described method and instrument is illustrated in FIG. 8 and is designated generally therein by reference numeral 50B.

The fastener 50B includes a generally U-shaped fastening member 60B and a receiver 62B. These two components are shown in the engaged orientation joining together tissue portions 54 and 52.

The fastening member 60B includes (1) a pair of anchoring means or legs 66B adapted to be passed through the tissue portions and (2) a link 68B which is connected to the legs 66B and which is adapted to lie substantially against one of the tissue portions (e.g., tissue portion 54 in FIG. 8). Each leg 66B of the fastening member 60B defines a plurality of spaced-apart, outwardly projecting, resilient locking teeth 80B on its exterior along at least a portion of its length. Each locking tooth 80B has an upper, horizontal flat locking surface 82B oriented generally normal to the longitudinal axis of the fastening member leg 66B and has a lower, slanted engagement surface 84B. Each locking tooth 80B is inwardly flexible when force is applied to the slanting surface 84B of the locking tooth 80B to act in a direction along the length of the leg 66B away from the distal end of the leg. However, each locking tooth 80B is resistant to inward flexing when force is applied to the surface 82B of the locking tooth to act in a direction along the length of the leg toward the distal end of the leg.

The receiver 62B defines passages 76B for receiving the fastening member legs 66B. The receiver 62B is also provided with a latch member 90B at each passage 76B. The latch member 90B defines (1) a slanted camming surface 92B for flexing each leg locking tooth 80B inwardly on one leg 66B of the fastening member 60B when the one leg is being inserted through the tissue portions and into the leg receiving passage 76B and (2) a retaining surface 94B for engaging one of the leg locking teeth 80B to prevent withdrawal of the leg from the receiver 62B after the leg has been received in the receiver as illustrated in FIG. 8.

The fastener 50B is applied to the tissue portions 54 and 52 in a manner substantially identical to that described above for the application of the first embodiment of the fastener 50A illustrated in FIGS. 1-7. If desired, the applier instrument 100 may be provided with a suitable cutter mechanism (not illustrated) to sever the portions of the fastening member legs 66B projecting beyond the bottom of the receiver 62B.

THIRD EMBODIMENT OF THE FASTENER

A third embodiment of a fastener that may be applied with the above-described method and instrument is illustrated in FIGS. 9 and 10 and is designated generally therein by reference numeral 50C.

The fastener 50C can be regarded as including two main components, a generally U-shaped or open looped fastening member 60C and a receiver 62C. The two components are maintained as unengaged, separate components prior to being applied to the tissue portions. In FIGS. 9 and 10, the two main components are shown in the engaged orientation joining together the tissue portions 54 and 52.

The fastener 50C may also be regarded, in one sense, as further including a leg guide member 200C (FIG. 9) for temporarily cooperating with the fastening member 60C and with the receiver 62C at the wound or incision when the fastening member and receiver are applied to the tissue portions. After application of the fastening member 60C and receiver 62C to the tissue portions, the leg guide member 200C is removed from the site and no longer forms a part of the structure of the assembled fastener 50C (FIG. 10).

As best illustrated in FIG. 9, the fastening member 60C includes (1) a pair of legs 66C adapted to be passed through the tissue portions and (2) a link 68C which is connected to the legs 66C and which is adapted to lie substantially against one of the tissue portions (e.g., tissue portion 54 in FIGS. 9 and 10). Before the fastening member 60C is applied to the time portions, the legs 66C of the fastening member 60C are generally parallel to each other and are generally perpendicular to the link 68C. Preferably, each leg 66C has a generally cylindrical configuration with a conical end 70C to facilitate or aid in the partial penetration of the tissue portions. The legs 66C may be solid or hollow.

The link 68C may have a generally cylindrical configuration as illustrated or may have any other suitable shape. Similarly, the legs 66C need not necessarily be cylindrical as illustrated but may have a non-circular cross-section. Preferably however, the legs are capable of being bent along the circumference of a relatively small circle into the orientation illustrated in FIGS. 9 and 10. To this end, it has been proposed that each leg 66C may be fabricated from a suitable material, such as an extruded 0.025 inch diameter rod of a thermoplastic polymer material.

The receiver 62C has a first side 71C which is adapted to be placed against one of the tissue portions and has an oppositely facing second side 73C. The receiver 62C further has a short central portion or member 72C joining a pair of leg receiving members 74C (designated in FIG. 9 only). Each leg receiving member 74C defines a first passage 76C extending between the receiver first side 71C and second side 73C for receiving a portion of one of the fastening member legs. Each receiving member 74C also defines a second passage 77C extending between the receiver first side 71C and second side 73C for receiving another portion of the same fastening member leg.

If the fastening member legs 66C have a cylindrical configuration as illustrated, then the receiving member passages 76C and 77C are preferably cylindrical bores of sufficient diameter to permit the legs 66C to be received therein. Each receiving member 74C, and the passages 76C and 77C defined therein, cooperate as means for receiving and encompassing at least portions of one of the fastening member legs 66C after the leg has been passed through the tissue portions as best illustrated in FIG. 9.

The guide member 200C has an engaging side 204C for contacting the second side 73C of the receiver 62C. The leg guide member 200C is disposed adjacent the second side 73C of the receiver 62C and is adapted to direct the distal end of each leg 66C of the fastening member 60C at the receiver second side 73C from the first passage 76C into the second passage 77C. The guide member 200C also functions to guide an intermediate portion of the leg extending between the receiver first passage 76C and the second passage 77C as relative movement is being effected between the fastening member 60C and the receiver 62C.

To this end, the guide member 200C includes a guide means for directing each leg 66C in the proper path and the guide means is defined in the guide member as a channel 206C opening to the engaging side 204C of the guide member 200C. As illustrated in FIG. 9, the bottom of the channel 206C is defined in the guide member 200C by a generally semi-cylindrical surface.

When joining the tissue portions 52 and 54 with the fastener 50C, the tissue portions are first approximated in face-to-face relationship as illustrated in FIG. 9. To apply the fastener 50C to join the tissue portions, the guide member 200C, along with the receiver 62C, is mounted in or on the anvil 130 of instrument 100 (illustrated in FIG. 5 and described above). The fastening member 60C is disposed in the instrument needles 102 on the other side of the tissue portions. The instrument 100 is then operated to effect relative movement between the needles 102 and the tissue portions so that the tissue portions are penetrated by the needles 102. Next, the drive members 120 are actuated to move the fastening member 60C along the needles 102 so that the fastening member legs 66C enter the receiver and guide member 200C to become properly engaged with the receiver 62C.

In any case, once the fastening member 60C has been driven through the needles 102 and properly engaged with the receiver 62C, the guide member 200C may be removed from the site of the wound or incision to leave the remaining fastener elements in the engaged orientation illustrated in FIG. 10 wherein the tissue portions 52 and 54 are joined together. The guide member 200C may be reused to apply another fastening member and receiver or may be discarded.

Although the guide member 200C is illustrated as being a separate element and may be regarded as being a temporary, removable portion of the fastener 50C, the guide member 200C may be integrally formed within the anvil 130 of the instrument 100 for applying the fastening member 60C and the receiver 62C. In such a case, the guide member 200C is properly characterized as not being one of the fastener components per se.

With the receiver design of the fastener 50C illustrated in FIGS. 9 and 10, it is seen that each of the fastening member legs 66C is bent along a radius and doubled back into an orientation wherein two portions of each leg are in parallel alignment. This unique configuration provides locking strength since force would be required to straighten out the legs in an attempt to disengage the fastening member 60C from the receiver 62C.

It is also to be noted from FIGS. 9 and 10 that the distal ends 70C of the fastening member legs 66C are directed back into the tissue portions. Only gently curving portions of the legs protrude below the receiver 62C. Thus, compared to the above-described second embodiment of the fastener (fastener 50B), the third embodiment of the fastener 50C has no sharp end portion at each leg projecting outwardly of the joined tissue portions where other surrounding tissue or organs may be damaged. Consequently, no portions of the legs of the fastening member 60C of the third embodiment of the fastener 50C need be severed to insure that an adjacent tissue or organ is not injured.

FOURTH EMBODIMENT OF THE FASTENER

A fourth embodiment of the fastener that may be applied with the above-described method and instrument is illustrated in FIG. 11 and is designated generally therein by reference numeral 50D. The fastener 50D is similar, and functions in a similar manner, to the third embodiment of the fastener 50C described above with reference to FIGS. 9 and 10. In addition, the fastener 50D includes the locking feature found in the second embodiment of the fastener 50B described above with reference to FIG. 8.

The elements of the fourth embodiment of the fastener 50D that are identical or functionally analogous to those of the second and third embodiments of the fasteners 50B and 50C, respectively, are designated by reference numerals identical to those used for the second and third embodiments with the exception that the fourth embodiment reference numerals are followed by the upper case letter D whereas the second and third embodiment reference numerals are followed by the upper case letters B and C, respectively.

The fastener 50D includes a fastening member 60D and a receiver 62B. The fastening member 60D is similar to the fastening member 60C of the third embodiment of the fastener 50C described above with reference to FIGS. 9 and 10 with the exception that the fastening member 60D has legs 66D that are formed with locking teeth 80D. Each locking tooth 80D has a locking surface 82B oriented generally normal to the longitudinal axis of the fastening member leg and has a slanted engagement surface 84D.

The receiver 62D is similar to the receiver 62C of the third embodiment of the fastener 50C described above with reference to FIGS. 9 and 10. The receiver 62D defines a first passage 76D and a second passage 77D for receiving each leg 66D of the fastening member 60D. In addition, the receiver 62D includes a latch member 90D associated with each second passage 77D. The latch member 90D defines (1) a camming surface 92D for flexing each leg locking tooth 80D inwardly on one leg when the one leg is being inserted into the receiver 62D and (2) a retaining surface 94D for engaging one of the locking teeth 80D on the leg to prevent withdrawal of the leg from the receiver 62D after the leg has been received therein.

The fourth embodiment of the fastener 50D is applied to the tissue portions with the instrument 100 in a manner analogous to that described above for the third embodiment of the fastener 50C illustrated in FIGS. 9 and 10. To this end, a guide member (identical to guide member 200C in FIG. 9) would be provided to temporarily engage the receiver 62D during application of the fastener 50D.

FIFTH EMBODIMENT OF THE FASTENER

The fifth embodiment of the fastener is illustrated in FIG. 12 and is designated generally therein by reference numeral 50E. The fastener 50E is similar, and functions in a similar manner, to the third embodiment of the fastener 50C described above with reference to FIGS. 9 and 10. The elements of the fifth embodiment of the fastener 50E that are identical or functionally analogous to those of the third embodiment of the fastener 50C are designated by reference numerals identical to those used for the third embodiment with the exception that the fifth embodiment reference numerals are followed by the upper case letter E whereas the third embodiment reference numerals are followed by the upper case letter C.

The fastener 50E includes a fastening member 60E and a receiver 62E. A guide member (not illustrated), similar to the guide member 200C illustrated in FIG. 9, is also initially provided for temporarily effecting application of the fastener 50E to the tissue portions 52 and 54.

The fastening member 60E is identical to the fastening member 60C of the third embodiment of the fastener 50C described above with reference to FIGS. 9 and 10. However, the receiver 62E differs somewhat from the receiver 62C of the third embodiment of the fastener 50C. Specifically, the receiver 62E, while defining a first passage 76E for each of the fastening member legs 66E, defines only one, central second passage 77E. The central passage 77E is adapted to receive the end portions of both of the fastening member legs 66E in side-by-side relationship as illustrated in FIG. 12.

The fastener 50E is applied to the tissue portions 54 and 52 in a manner substantially identical to that described above for the application of the third embodiment of the fastener 50C illustrated in FIGS. 9 and 10.

SIXTH EMBODIMENT OF THE FASTENER

Figure 13:
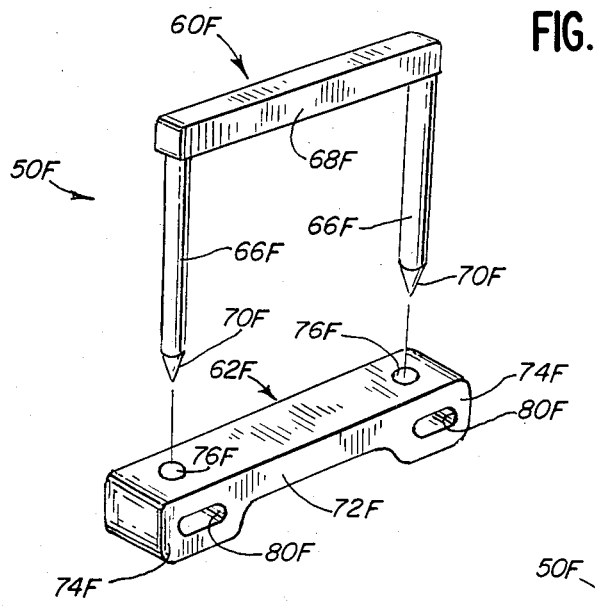
FIG. 13 is a exploded, perspective view of a sixth embodiment of a fastener.
Figure 14:
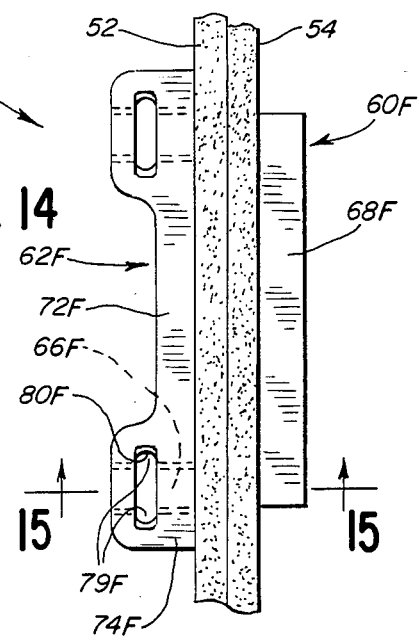
FIG. 14 is an enlarged, fragmentary, cross-sectional view of two portions of mammalian tissue defined by an incision or wound and being held together by the sixth embodiment of the fastener illustrated in FIG. 13 wherein the fastening member legs have been severed flush with the receiver.
Figure 15:
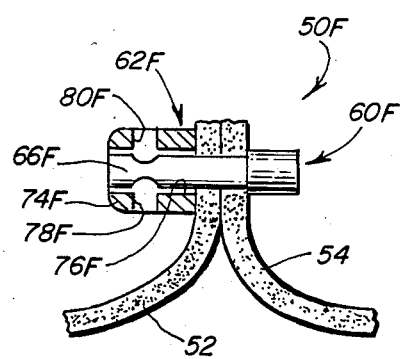
FIG. 15 is a fragmentary, cross-sectional view taken along the plane 15—15 in FIG. 14.

The sixth embodiment of the fastener is illustrated in FIGS. 13-15 and is designated generally therein by reference 50F. The fastener 50F includes a fastening member 60F and a receiver 62F. The fastener 50F is similar, in some respects, to the first embodiment of the fastener 50A described above with reference to FIGS. 1-3. The elements of the sixth embodiment of the fastener 50F that are functionally analogous to those of the first embodiment of the fastener 50A are designated by reference numerals identical to those used for the first embodiment with the exception that the sixth embodiment reference numerals are followed by the upper case letter F whereas the first embodiment reference numerals are followed by the upper case letter A.

As is best illustrated in FIG. 13, the fastening member 60F includes (1) a pair of legs 66F adapted to be passed through the tissue portions and (2) a link 68F which is connected to the legs 66F and which is adapted to lie substantially against one of the tissue portions (e.g., tissue portion 54 in FIG. 14). The legs 66F of the fastening member 60F are generally parallel to each other and are generally perpendicular to the link 68F. Preferably, each leg 66F has a solid, generally cylindrical configuration with a conical end 70F. The link 68F may have the rectangular parallelpiped shape illustrated or may have any other suitable shape.

The receiver 62F includes a central member 72F joining a pair of leg receiving members 74F. Each leg receiving member 74F defines at least one passage 76F for receiving one of the fastening member legs 66F as best illustrated in FIG. 14. If the fastening member legs 66F have a cylindrical configuration as illustrated, then the receiving member passages 76F are preferably cylindrical bores of sufficient diameter to permit the legs 66F to be received (loosely or in sliding engagement). Each receiving member 74F and the passage 76F defined therein cooperate as means for receiving and encompassing at least a portion of one of the fastening members legs 66F after the leg has been passed through the tissue portions as best illustrated in FIGS. 14 and 15.

Preferably, each receiving member 74F of the receiver 62F defines a first aperture 78F (FIG. 15 only) communicating from the exterior of the receiving member 74F with the interior of the passage 76F. Also, a second aperture 80F (FIGS. 13-15) is provided in each receiving member 74F opposite the first aperture 78F for communicating between the exterior of the receiving member 74F and the interior of the passage 76F. At least one of these two apertures 78F and 80F is intended to accommodate the insertion of a ram-like member of the applying instrument for deforming the fastening member leg 66F in a manner described in detail hereinafter. The other of the apertures 78F and 80F may function as a guide or detent to position the receiver 62F within the instrument.

The fastening member 60F and the receiver 62F may be formed from suitable materials, such as themoplastic polymer materials that are absorbable by mammalian tissue.

To apply the fastener 50F to join the tissue portions, the receiver 62F is mounted in or on the anvil 130 of the instrument 100 (illustrated in FIG. 5 and described above). The fastening member 60F is disposed in the instrument needles 102 on the other side of the tissue portions. The instrument 100 is then operated to effect relative movement between the needles 102 and the tissue portions so that the tissue portions are penetrated by the needles. Next, the drive members 120 are actuated to move the fastening member 60F along the needles 102 so that the fastening member legs 66F enter the receiver 62F. The relative movement between the fastening member 60F and the receiver 62F is terminated when the fastening member link 68F is at a desired distance from the receiver 62F to secure the tissue portions together. Preferably, this movement is terminated after the tissue portions have been compressed together a desired amount.

At this point, the distal ends of the fastening member legs 66F will typically protrude from the receiver opposite the side of the receiver that is contacting one of the tissue portions. In FIG. 14, the legs 66F are not shown protruding beyond the receiver 62F since, in accordance with a preferred further step of the method, the protruding portions have been severed to leave the leg ends flush with the receiver 62F.

Regardless of whether or not the protruding portions of the fastening member legs 66F are severed, the fastening member legs 66F and/or the receiver 62F are acted upon in a certain member to effect an engagement of the legs 66F with the receiver 62F to hold the two tissue portions together. To this end, each fastening member leg 66F is deformed or coined to force a bulged out portion 79F of each fastening member leg 66F into engagement with the receiver 62F.

The instrument 100 may be modified to include means for effecting this deformation (which means are not illustrated in FIG. 5). In particular, the anvil 130 illustrated in FIG. 5 would be incorporated in a lower jaw of the instrument. The lower jaw would also house a fastening member leg deforming and severing mechanism. Such a mechanism would include a pair of deforming members adapted to reciprocate within the lower jaw. After the fastening member legs 66F have been pushed the desired amount into the receiver 62F, the instrument deforming members would be actuated to enter the apertures 78F (or 80F or both). This deforms the portion 79F of each leg.

To accomodate the deformation of each leg portion 79F, the apertures 78F and 80F each have a dimension (measured normal to the longitudinal axis of the passage 76F) that is greater than the dimension of the passage 76F (measured normal to the longitudinal axis of the passage). In the embodiment illustrated in FIGS. 13-15, the apertures 78F and 80F, when viewed from the side, are seen to each have a generally rectantular configuration (with somewhat rounded corners) with a length greater than the diameter of the cylindrical bore passage 76F. This accommodates the bulged out portion 79F of the fastening member leg and thus effects a rivet-like engagement of the leg 66F with the receiver 62F.

It has been found that the above-described method of applying the fastener 50F to the tissue portions results in a relatively strong retention structure comprising the fastening member 60F and engaged receiver 62F. Further, one size fastener 50F may be used for a variety of different tissue thicknesses since the fastening member 60F can be inserted into the receiver 62F to a selected depth for the desired amount of tissue compression and the legs 66F can then be deformed to effect the engagement of the legs and receiver. This deformation can take place at any point along the length of each leg 66F, depending on tissue thickness. Such a fastener structure and method of applying the fastener readily accommodates application of the fastener 50F by means of a suitable instrument that can be designed to apply a plurality of such fasteners simultaneously.

With the embodiment of the fastener 50F described above, the legs 66F are deformed into engagement with the receiver 62F. However, it is to be understood that the legs 66F may be formed with apertures or notches (not illustrated) and that portions of the receiver 62F may be deformed into the leg notches or apertures for effecting the engagement between the receiver 62F and fastening member 60F. Further, a combination of both the deformation of the receiver 62F and the deformation of the legs 66F may also be used to effect engagement of the receiver 62F and fastening member 60F.

With the above-described method, the protruding portions of the fastening members legs 66 may be severed during or after the step of deforming the legs 66F and/or receiver 62F. Preferably, during the step of severing the protruding portions of the fastening member legs 66F, the protruding portions of the fastening member legs are surrounded with a suitable container for catching the leg protruding portions after they are severed so as to prevent the severed portions of legs from falling into the surrounding tissue or body cavity. This container may be part of the instrument 100.

The material from which the fastening member legs 66F are formed is preferably one that is relatively easily deformable to accommodate the deforming action of the instrument. If just the legs are to be deformed, the receiver 62A need not be fabricated from such a relatively easily deformable material.

Regardless of the materials selected for the fastening member 60F and receiver 62F, it may be desirable to effect the method of deforming the fastening legs 66F and/or receiver 62F with the aid of heat to soften the material. Such heat may be provided by a suitable process (e.g., electrical resistance heating). Such heating would reduce the magnitude of the mechanical forces required to effect the necessary deformation.

Although the instrument 100 would preferably include cutting blades (not illustrated) for severing the projecting portions of the legs 66F as described above, in some applications it may not be desired to sever the legs. In such applications, it would, of course, not be necessary to equip the instrument 100 with cutting blades.

SEVENTH EMBODIMENT OF THE FASTENER

The seventh embodiment of the fastener is illustrated in FIG. 16 and is designated generally therein by reference numeral 50G. The fastener 50G is of the type that includes at least a fastening member 60G. Additionally, the fastener 50G may optionally include a receiver 62G. These two components are illustrated separately in FIG. 16.

The fastening member 60G has a pair of legs 66G joined by a link 68G. Each fastening member leg 66G has two ends and each leg is connected intermediate of the leg ends to the link 68G.

As illustrated in FIG. 16, the legs 66G are of a generally cylindrical configuration and the link 68G is also generally cylindrical. However, other suitable shapes may be employed. The fastening member 60G is fabricated from a suitable thermoplastic material so that the legs 66G can be temporarily flexed or bent during application of the fastening member by means described hereinafter detail. Similarly, the link 68G if designed to accommodate a bending or flexing of the link.

The receiver 62G is generally flexible and is preferably fabricated with a mesh-like construction that can be penetrated by needles. The overall configuration of the receiver 62G is planar or plate-like and the receiver 62G may have rounded corners rather than the right angle corners illustrated.

The fastener 50G may be applied by the instrument 100 described above with reference to FIG. 5. To this end, the length of the fastening member link 68G is substantially greater than the distance between the instrument needles 102. This accommodates the insertion of the fastening member 60G in the needles 102 as illustrated in FIG. 17.

When applying the fastener 50G to the tissue portions 52 and 54 as illustrated in FIG. 17, the tissue portions are first arranged in face-to-face relationship. Then, the receiver 62G is disposed against one of the tissue portions (tissue portion 52 in FIG. 17) opposite the needles 102. The receiver 62G is preferably held against the tissue portion by means of a guide member 200G which may be formed as part of the instrument anvil 130 or which may be a separate, removable member that is temporarily held in place by the anvil 130.

The guide member 200G has an engaging side 204G for contacting a side of the receiver 62G. The leg guide member 200G also defines a channel 206G opening to the engaging side 204G of the guide member. The bottom of the channel 206G is preferably defined in the guide member 200G by a curved surface as illustrated.

The receiver 62G is held tightly against the tissue portion 52 by the guide member 200G which is forced toward the tissue portions with a force $F_2$ by the anvil 130 of the instrument 100. The instrument is then further actuated to push the needles 102 downwardly through both the tissue portions 54 and 52 and receiver 62G from one side of the wound or incision until the distal ends of the needles engage the receiver channel 206G as illustrated in FIG. 18. With relative movement between the needles 102 and the guide member 200G thus terminated, the discharge openings of the needles are located on the other side of the wound or incision below the receiver 62G.

Before, during, or after the step of penetrating the tissue portions and the receiver 62G with the needles, the fastening member 60G is loaded into the needles 102 through the receiving openings (openings 112 in FIG. 5) so that the link 68G extends through the needle slots (slots 114 in FIG. 6) between the needles. Next, the fastening member 60G is urged along the needles 102 by means of the drive members 120 as illustrated in FIG. 18 to locate at least a portion of the link 68G on one side of the wound or incision adjacent one of the tissue portions (54 in FIG. 18) and to locate and secure at least a portion of each of the legs 66G on the other side of the wound or incision adjacent another of the tissue portion (portion 52).

As the fastening member 60G is urged along the needles 102, the leading ends of the fastening member legs 66G impinge upon the channel 206G of the guide member 200G and are flexed, temporarily deformed, or bent inwardly below the receiver 62G. Ultimately, each of the legs 66G is discharged from the needle completely on the other side of the wound or incision below the receiver 62G. Subsequently, the needles 102 are withdrawn from the receiver 62G and from the tissue portions 52 and 54 with the fastener 50G remaining in the configuration as illustrated in FIG. 19 to hold together the tissue portions.

If desired, the fastener 50G may be used without the receiver 62G. In such a situation, the process of applying the fastening member 60G to the tissue portions is substantially the same as described above with reference to FIGS. 17-19 except that the guide member 200G is placed directly against the tissue portion 52.

To accommodate different tissue thicknesses, the instrument 100 may be provided with a mechanism (not illustrated) for varying the distance between the needles 102. For example, if the needles are moved closer together, tissues of greater thicknesses may be fastened with a given size fastener.

Although the method and instrument 100 have been described above with respect to the application of any one of a variety of fasteners, it is to be realized that the instrument 100 may be modified to apply a plurality of fasteners simultaneously. For example, the instrument 100 could be fabricated with a plurality of pairs of needles and cooperating anvils.

ALTERNATIVE DESIGN FEATURES

In FIGS. 1-15, the two legs of each fastening member are connected by a portion of the fastening member (e.g., the link or clamping member) which is illustrated as being generally straight and extending perpendicular to the two legs. The structure need not be limited to such a shape however. Instead, all or a portion of the length of the fastening member between the two legs may be arched or arcuate or may include an arcuate portion (e.g., an inverted U-shaped configuration). This would function to initially provide a free space between the upper tissue portion and the top of the fastening member to allow for some expansion of the tissue.

However, in those situations where increased initial tissue compression is desired, a modified receiver structure may be provided to cooperate with the above-described arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

From the foregoing, it will be observed that numerous variations and modifications may be effected without departing from the true spirit and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A method for applying a fastener to close a wound or incision in mammalian tissue by holding together portions of said tissue defining the wound or incision so as to facilitate healing of the wound or incision, said fastener being of the type comprising at least a fastening member and a receiver, said fastening member having a pair of legs joined by a link, said receiver being adapted to receive at least portions of said fastening member legs so that said fastener can remain in said tissue portions with at least a portion of said link lying substantially against one of said tissue portions on a first side of the wound or incision, with the receiver lying against other of said tissue portions on a second side of the wound or incision and with at least a portion of each of said legs being received in said receiver and being secured thereto, said method comprising the steps of:
   (a) approximating said tissue portions in generally face-to-face relationship;
   (b) providing a pair of spaced-apart needles, that are oriented in generally parallel planes, each needle having a distal end adapted for piercing said tissue portions, each needle being hollow and having a passage extending along its length from a fastener receiving opening to a discharge opening a said distal end, and each said needle defining a slot extending along its length in communication with said passage and facing the slot in the other needle;
   (c) providing an anvil to hold at least said receiver adjacent said other tissue portion on said second side of said wound or incision;
   (d) placing a leg guide member on said anvil;
   (e) placing said receiver on said leg guide member;
   (f) moving said anvil toward said needles to urge said receiver against said other tissue portion;
   (g) inserting said needles through said approximated tissue portions to
      (1) locate said receiving openings on said first side of said wound or incision, and
      (2) locate at least portions of said discharge openings on said second side of said wound or incision;
   (h) before, during, or after step (g), loading said fastening member into said needles through said receiving openings with
      (1) each of said legs being disposed in one of said needle passages and
      (2) said link extending through said needle slots between said needles;
   (i) urging said fastening member along said needles to
      (1) locate at least a portion of said link on said first side of said wound or incision adjacent said one tissue portion, and
      (2) locate and secure at least a portion of each said leg on said second side of said wound or incision adjacent said other tissue portion; and
   (j) withdrawing said needles from said tissue portions whereby the fastener remains holding together said tissue portions.

* * * * *